(12) United States Patent  
Opolski et al.

(10) Patent No.: US 7,473,260 B2
(45) Date of Patent: Jan. 6, 2009

(54) SUTURE SEVER TUBE

(75) Inventors: Steven Opolski, Carlisle, MA (US); Sean Forde, Watertown, MA (US)

(73) Assignee: NMT Medical, Inc., Boston, MA (US)

(*) Notice: Subject to any disclaimer, the term of this patent is extended or adjusted under 35 U.S.C. 154(b) by 651 days.

(21) Appl. No.: 10/862,939

(22) Filed: Jun. 8, 2004

(65) Prior Publication Data
US 2005/0059983 A1 Mar. 17, 2005

Related U.S. Application Data

(60) Provisional application No. 60/501,949, filed on Sep. 11, 2003.

(51) Int. Cl.
*A61B 17/04* (2006.01)

(52) U.S. Cl. ........................ 606/148; 606/170

(58) Field of Classification Search ................ 606/208, 606/209, 139, 144, 148, 170
See application file for complete search history.

(56) References Cited

U.S. PATENT DOCUMENTS

| 3,683,892 | A |  | 8/1972 | Harris |  |
|---|---|---|---|---|---|
| 3,874,388 | A |  | 4/1975 | King et al. | 128/334 R |
| 3,990,144 | A |  | 11/1976 | Schwartz | 30/123 |
| 4,007,743 | A |  | 2/1977 | Blake | 128/334 R |
| 4,038,988 | A |  | 8/1977 | Perisse | 606/139 |
| 4,069,825 | A |  | 1/1978 | Akiyama |  |
| 4,246,698 | A |  | 1/1981 | Lasner et al. | 30/134 |
| 4,271,838 | A |  | 6/1981 | Lasner et al. | 606/138 |
| 4,384,406 | A |  | 5/1983 | Tischlinger | 606/138 |
| 4,452,246 | A |  | 6/1984 | Bader et al. | 606/147 |
| 4,494,542 | A |  | 1/1985 | Lee | 606/138 |
| 4,799,483 | A |  | 1/1989 | Kraff | 606/226 |
| 4,836,204 | A |  | 6/1989 | Landymore et al. | 128/334 R |
| 4,932,963 | A |  | 6/1990 | Ritter et al. | 606/224 |
| 4,963,147 | A | * | 10/1990 | Agee et al. | 606/170 |
| 4,984,941 | A |  | 1/1991 | White et al. | 408/104 |
| 4,986,825 | A | * | 1/1991 | Bays et al. | 604/22 |

(Continued)

FOREIGN PATENT DOCUMENTS

DE 9214580 3/1994

(Continued)

OTHER PUBLICATIONS

International Search Report for PCT/US04/18119, mailed on Nov. 10, 2004 (5 pages).

(Continued)

*Primary Examiner*—Darwin P Erezo
(74) *Attorney, Agent, or Firm*—K&L Gates LLP

(57) ABSTRACT

An apparatus for cutting a suture. In one embodiment the suture cutting apparatus includes a distal cutting end and a proximal control end. The apparatus also includes a first tube defining a lumen, and a second tube located and movable within the lumen of the first tube. The second tube defines a lumen and includes a lever arm pivotably attached at the distal cutting end of the apparatus. The lever arm has a cutting edge that is held away from the longitudinal axis of the second tube when the lever arm is located within the first tube, and is biased toward the longitudinal axis of second tube when the lever arm is outside of the first tube.

21 Claims, 10 Drawing Sheets

U.S. PATENT DOCUMENTS

| | | | |
|---|---|---|---|
| 5,108,420 A | 4/1992 | Marks | 606/213 |
| 5,122,152 A | 6/1992 | Mull | 606/170 |
| 5,192,301 A | 3/1993 | Kamiya et al. | 606/213 |
| 5,242,459 A | 9/1993 | Buelna | |
| 5,284,488 A | 2/1994 | Sideris | 606/213 |
| 5,286,255 A * | 2/1994 | Weber | 604/22 |
| 5,292,327 A | 3/1994 | Dodd et al. | |
| 5,301,684 A * | 4/1994 | Ogirala | 600/567 |
| 5,312,341 A | 5/1994 | Turi | 604/96 |
| 5,318,589 A * | 6/1994 | Lichtman | 606/205 |
| 5,334,217 A | 8/1994 | Das | 606/213 |
| 5,346,500 A | 9/1994 | Suchart | 606/138 |
| 5,376,096 A * | 12/1994 | Foster | 606/147 |
| 5,417,700 A | 5/1995 | Egan | 606/144 |
| 5,425,744 A | 6/1995 | Fagan et al. | 606/213 |
| 5,433,727 A | 7/1995 | Sideris | 606/213 |
| 5,443,475 A * | 8/1995 | Auerbach et al. | 606/170 |
| 5,451,235 A | 9/1995 | Lock et al. | 606/213 |
| 5,496,331 A | 3/1996 | Xu et al. | |
| 5,507,811 A | 4/1996 | Koike et al. | 623/11 |
| 5,620,461 A | 4/1997 | Muijs Van De Moer et al. | 606/213 |
| 5,634,936 A | 6/1997 | Linden et al. | 606/213 |
| 5,649,947 A * | 7/1997 | Auerbach et al. | 606/170 |
| 5,683,411 A | 11/1997 | Kavteladze et al. | 606/200 |
| 5,702,421 A | 12/1997 | Schneidt | 606/213 |
| 5,709,707 A | 1/1998 | Lock et al. | 606/213 |
| 5,725,552 A | 3/1998 | Kotula et al. | 606/213 |
| 5,733,294 A | 3/1998 | Forber et al. | 606/151 |
| 5,741,297 A | 4/1998 | Simon | 606/213 |
| 5,759,188 A * | 6/1998 | Yoon | 606/147 |
| 5,797,907 A | 8/1998 | Clement et al. | |
| 5,797,939 A * | 8/1998 | Yoon | 606/167 |
| 5,797,958 A * | 8/1998 | Yoon | 606/207 |
| 5,800,516 A | 9/1998 | Fine et al. | 623/1 |
| 5,810,884 A | 9/1998 | Kim | 606/213 |
| 5,853,422 A | 12/1998 | Huebsch et al. | 606/213 |
| 5,860,993 A | 1/1999 | Thompson et al. | 606/148 |
| 5,861,003 A | 1/1999 | Latson et al. | 606/213 |
| 5,879,366 A | 3/1999 | Shaw et al. | 606/213 |
| 5,893,863 A * | 4/1999 | Yoon | 606/170 |
| 5,904,703 A | 5/1999 | Gilson | 606/213 |
| 5,908,429 A * | 6/1999 | Yoon | 606/144 |
| 5,919,200 A | 7/1999 | Stambaugh et al. | 606/159 |
| 5,928,250 A | 7/1999 | Koike et al. | 606/139 |
| 5,944,738 A | 8/1999 | Amplatz et al. | 606/213 |
| 5,976,174 A | 11/1999 | Ruiz | 606/213 |
| 5,984,939 A * | 11/1999 | Yoon | 606/170 |
| 5,993,475 A | 11/1999 | Lin et al. | 606/213 |
| 6,024,756 A | 2/2000 | Huebsch et al. | 606/213 |
| 6,051,004 A | 4/2000 | Gill | 606/147 |
| 6,056,760 A | 5/2000 | Koike et al. | 606/148 |
| 6,063,096 A | 5/2000 | Boebel et al. | |
| 6,077,277 A * | 6/2000 | Mollenauer et al. | 606/144 |
| 6,077,291 A | 6/2000 | Das | 606/213 |
| 6,080,182 A | 6/2000 | Shaw et al. | 606/213 |
| 6,086,606 A * | 7/2000 | Knodel et al. | 606/208 |
| 6,110,127 A | 8/2000 | Suzuki | |
| 6,113,609 A | 9/2000 | Adams | 606/139 |
| 6,117,159 A | 9/2000 | Huebsch et al. | 606/213 |
| 6,171,329 B1 | 1/2001 | Shaw et al. | 606/213 |
| 6,174,322 B1 | 1/2001 | Schneidt | 606/213 |
| 6,206,907 B1 | 3/2001 | Marino et al. | 606/215 |
| 6,214,029 B1 | 4/2001 | Thill et al. | 606/213 |
| 6,221,092 B1 | 4/2001 | Koike et al. | 606/213 |
| 6,270,515 B1 | 8/2001 | Linden et al. | 606/213 |
| 6,290,674 B1 | 9/2001 | Roue et al. | 604/107 |
| 6,312,446 B1 | 11/2001 | Huebsch et al. | 606/213 |
| 6,322,548 B1 | 11/2001 | Payne et al. | 604/500 |
| 6,355,052 B1 | 3/2002 | Neuss et al. | 606/213 |
| 6,375,671 B1 | 4/2002 | Kobayashi et al. | 606/213 |
| 6,379,368 B1 | 4/2002 | Corcoran et al. | 606/153 |
| 6,387,104 B1 | 5/2002 | Pugsley, Jr. et al. | 606/139 |
| 6,402,772 B1 | 6/2002 | Amplatz et al. | 606/200 |
| 6,440,152 B1 | 8/2002 | Gainor et al. | 606/213 |
| 6,482,224 B1 | 11/2002 | Michler et al. | 606/219 |
| 6,494,888 B1 | 12/2002 | Laufer et al. | 606/153 |
| 6,551,344 B2 | 4/2003 | Thill | 606/213 |
| 6,596,013 B2 | 7/2003 | Yang et al. | 606/215 |
| 6,623,508 B2 | 9/2003 | Shaw et al. | 606/213 |
| 2002/0010481 A1 | 1/2002 | Jayaraman et al. | 606/151 |
| 2002/0019648 A1 | 2/2002 | Akerfeldt et al. | 606/213 |
| 2002/0026208 A1 | 2/2002 | Roe et al. | 606/190 |
| 2002/0052572 A1 | 5/2002 | Franco et al. | 604/8 |
| 2002/0077555 A1 | 6/2002 | Schwartz | 600/486 |
| 2002/0087178 A1 | 7/2002 | Nobles et al. | 606/167 |
| 2002/0096183 A1 | 7/2002 | Stevens et al. | 128/898 |
| 2002/0107531 A1 | 8/2002 | Schreck et al. | 606/142 |
| 2002/0183786 A1 | 12/2002 | Girton | 606/213 |
| 2002/0183787 A1 | 12/2002 | Wahr et al. | 606/213 |
| 2003/0009195 A1 | 1/2003 | Field et al. | 606/219 |
| 2003/0028213 A1 | 2/2003 | Thill et al. | 606/200 |
| 2003/0045893 A1 | 3/2003 | Ginn | 606/151 |
| 2003/0050665 A1 | 3/2003 | Ginn | 606/215 |
| 2003/0059640 A1 | 3/2003 | Marton et al. | 428/544 |
| 2003/0100920 A1 | 5/2003 | Akin et al. | 606/213 |
| 2003/0109891 A1 | 6/2003 | Dana et al. | 606/148 |
| 2003/0120287 A1 | 6/2003 | Gross et al. | 606/148 |
| 2003/0139819 A1 | 7/2003 | Beer et al. | 623/23 |
| 2003/0181926 A1 | 9/2003 | Dana et al. | 606/148 |
| 2003/0195530 A1 | 10/2003 | Thill | 606/151 |
| 2004/0097865 A1 | 5/2004 | Anderson et al. | 604/22 |
| 2004/0267306 A1 | 12/2004 | Blaeser et al. | |

FOREIGN PATENT DOCUMENTS

| | | |
|---|---|---|
| DE | 43 14 463 | 11/1994 |
| DE | 19905311 | 8/1999 |
| EP | 1222897 | 7/2002 |
| WO | WO 98/07375 | 2/1998 |
| WO | WO 99/18862 | 4/1999 |
| WO | WO 99/18864 | 4/1999 |
| WO | WO 99/18870 | 4/1999 |
| WO | WO 99/18871 | 4/1999 |
| WO | WO 01/78596 | 10/2001 |
| WO | WO03/059174 | 7/2003 |
| WO | WO 03/077733 | 9/2003 |

OTHER PUBLICATIONS

Written Opinion for PCT/ US04/18119, mailed on Nov. 10, 2004 (8 pages).

International Preliminary Report on Patentability for PCT/US2004/018119, mailed on Mar. 23, 2006 (10 pages).

* cited by examiner

SUTURE SEVER TUBE

REFERENCE TO RELATED APPLICATIONS

This application claims priority to and benefit of U.S. Provisional Patent Application No. 60/501,949, filed Sep. 11, 2003, the entire disclosure of which is incorporated by reference herein.

FIELD OF THE INVENTION

The invention relates to medical instruments for cutting sutures in general and more particularly to devices for cutting sutures remotely such as sutures secured to an intracardiac septal occluder implanted in a patient by a percutaneous route.

BACKGROUND

Sutures, as components of a percutaneous delivery system, can provide the system with a method to remotely control an implant, such as an intracardiac septal occluder, during implantation. Since it is not uncommon for a delivery system to be four feet long or more in order to traverse a vessel, any suture that might extend through the delivery system would be at least as long. In a case where this suture needs to be released from the implant to which it is tethered following remote placement of the implant, it would be undesirable and possibly disruptive to the implant's integrity and position, to disengage the suture by unthreading an entire four feet of suture through the implant. A more desirable, and less disruptive approach, might be to remotely sever the suture, adjacent to the implant, to allow for efficient unthreading of a shorter section of the suture from the implant.

SUMMARY OF THE INVENTION

The invention generally relates to an apparatus for cutting a suture. More particularly, an apparatus for cutting sutures remotely such as sutures secured to an intracardiac septal occluder implanted in a patient by a percutaneous route.

In one aspect, the invention relates to a suture cutting apparatus including a distal cutting end and a proximal control end. The distal cutting end further includes a first tube defining a lumen, and a second tube, located and slideably movable within the lumen of the first tube, the second tube defining a lumen and further including a cutting edge.

In a particular embodiment, the apparatus includes a lever arm having a proximal end and a distal end, and a second tube with a slot for receiving the lever arm. In a further embodiment of the apparatus, the lever arm contains a pivot positioned on the lever arm. In one embodiment, the lever arm is pivotably attached to the distal cutting end of the second tube. Alternatively, the lever arm is flexibly attached to the distal cutting end of the second tube. In one embodiment of the apparatus including a lever arm, the cross section of the lever arm is generally U-shaped.

In a further embodiment of the apparatus including a lever arm, the cutting edge may be positioned on the distal end of the lever arm. In still another embodiment, the lever arm is parallel to the longitudinal axis of the second tube while the lever arm is located within the lumen of the first tube, and forms an angle relative to the longitudinal axis of the second tube while the lever arm is outside the lumen of the first tube. The angle is in the range of 0-90°. In one embodiment, while the lever arm is outside the lumen of the first tube, the cutting edge is angled towards the longitudinal axis of the second tube. Alternatively, the cutting edge is substantially perpendicular to the longitudinal axis of the second tube. In yet another embodiment of the apparatus, the cutting edge may be replaceable.

In still another embodiment, the apparatus includes a return guide. The return guide may be positioned on the lever arm and slideably movable within the first tube.

In a further embodiment, the apparatus includes a catheter.

In another aspect, the invention provides a method for cutting a suture. The method includes providing an apparatus with a distal cutting end and a proximal control end, the distal cutting end including a first tube defining a lumen and, and a second tube. The second tube is located and slideably movable within the lumen of the first tube. The second tube defines a lumen and includes a cutting edge. The second tube is moved to engage the cutting edge with the suture. In one embodiment of the invention, engaging the cutting edge with the suture sections the suture into two segments.

In still another embodiment, the apparatus is advanced through a catheter positioned in a patient's body. In a further embodiment, the suture is joined to an intracardiac septal occluder.

BRIEF DESCRIPTION OF THE DRAWINGS

The aspects of the invention presented above and many of the accompanying advantages of the present invention will become better understood by referring to the included drawings, which show a system according to the invention and in which.

DESCRIPTION

The present invention pertains to an apparatus for cutting a suture. The apparatus may be used to deliver implants, e.g., intracardiac occluders, for example, intracardiac septal occluders manufactured by NMT Medical Inc., Boston, Mass. Intracardiac occluders are used to repair congenital or acquired defects in the heart or the major blood vessels, thereof, including interatrial septal shunts, such as a patent foramen ovale, interventricular septal shunts, patent ductus arteriosus and aortic-pulmonary window.

Figure 1:
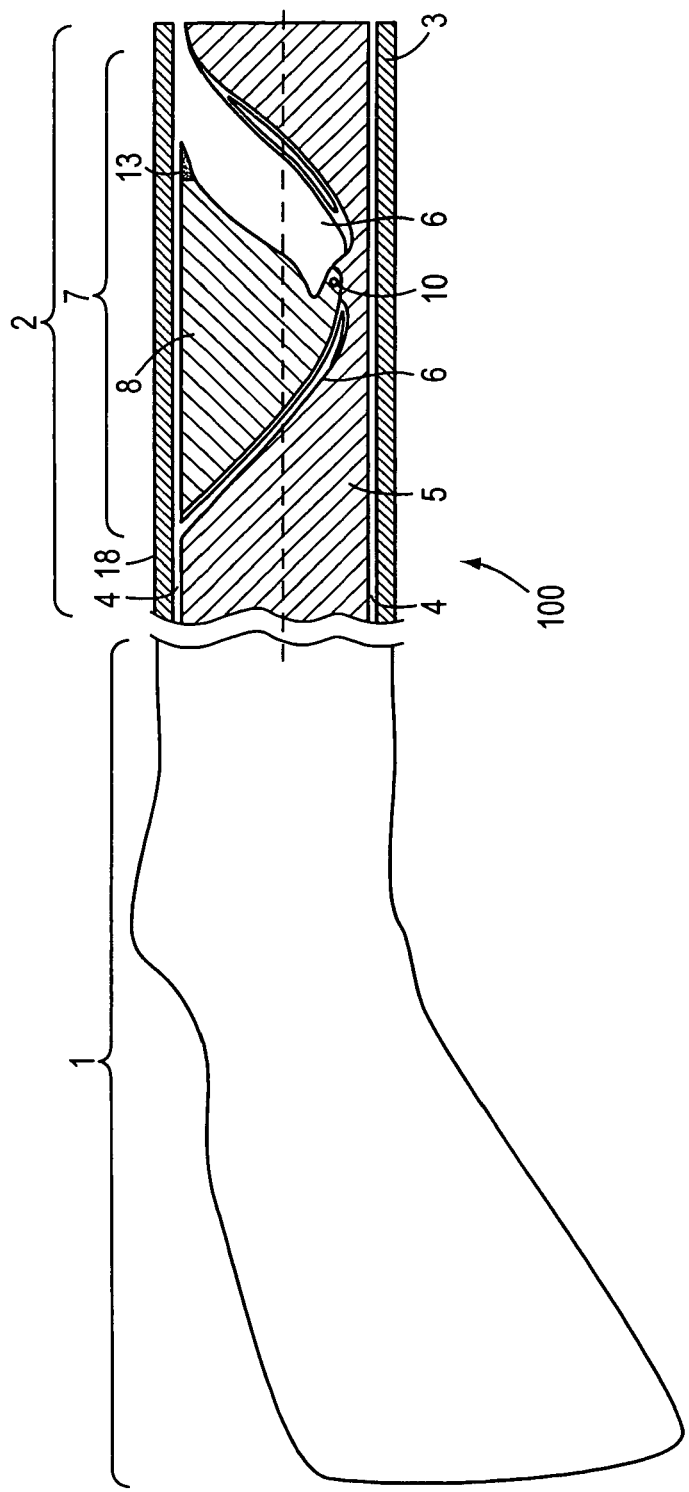
FIG. 1 is a schematic of the apparatus with a cutaway schematic of the first tube according to an illustrative embodiment of the invention.

FIG. 1 is an illustrative schematic of the apparatus 100 with a cutaway schematic of the first tube according to an illustrative embodiment of the invention. In one aspect, the invention relates to an apparatus for remotely severing a suture. The exemplary apparatus 100 for cutting a suture includes a proximal control end 1 and a distal cutting end 2. The proximal control end 1 is the end proximal to the operator and used to control the distal cutting end 2. The apparatus 100 also includes a first tube 3, a second tube 5, a lever arm 8, a cutting edge 13, and a pivot 10. In some embodiments, according to the invention, the distal cutting end further includes a return guide (not shown) and/or a spring mechanism (not shown).

The distal cutting end 2 of the apparatus 100 for remotely cutting a suture includes a portion of the first tube 3 including a first lumen 4. A second tube 5 is longitudinally disposed within the first lumen 4 of the first tube 3. The second tube 5 includes a longitudinally disposed lumen 6 extending from the proximal control end 1 of the apparatus 100 to the distal cutting end 2 of the apparatus 100. The second tube 5 is slidably moveable within the first lumen 4 of the first tube 3. The first tube 3 is generally elongated and has an external diameter sufficiently sized, e.g., a diameter 0.03 mm and a length approximately 150 cm, to allow the first tube 3 to be delivered percutaneously via a vessel to an anatomical site, for example, the atrial septum, in a patient. The first lumen 4 is hollow, typically cylindrically shaped, and has an internal diameter slightly larger than the external diameter of the second tube 5 to allow the second tube 5 to slide within the first lumen 4. The second tube 5 is elongated and has an internal diameter sized to allow the hollow and cylindrical second lumen 6 to pass a suture, for example, single 0 catgut, polyethylene or nylon suture. The second tube 5 also contains a slot 7 sized and shaped to receive the lever arm 8 pivotably attached to the second tube 5. In one embodiment, the first tube 3 is longitudinally and slidably disposed within a catheter 18. In another embodiment, the first tube 3 serves as the catheter 18. Materials for construction of the apparatus include but are not limited to polyethylene block copolymer (Pebax®), polytetrafluoroethylene (PTFE), metals such as stainless steel, a ceramic, or a composite material.

Figure 2:
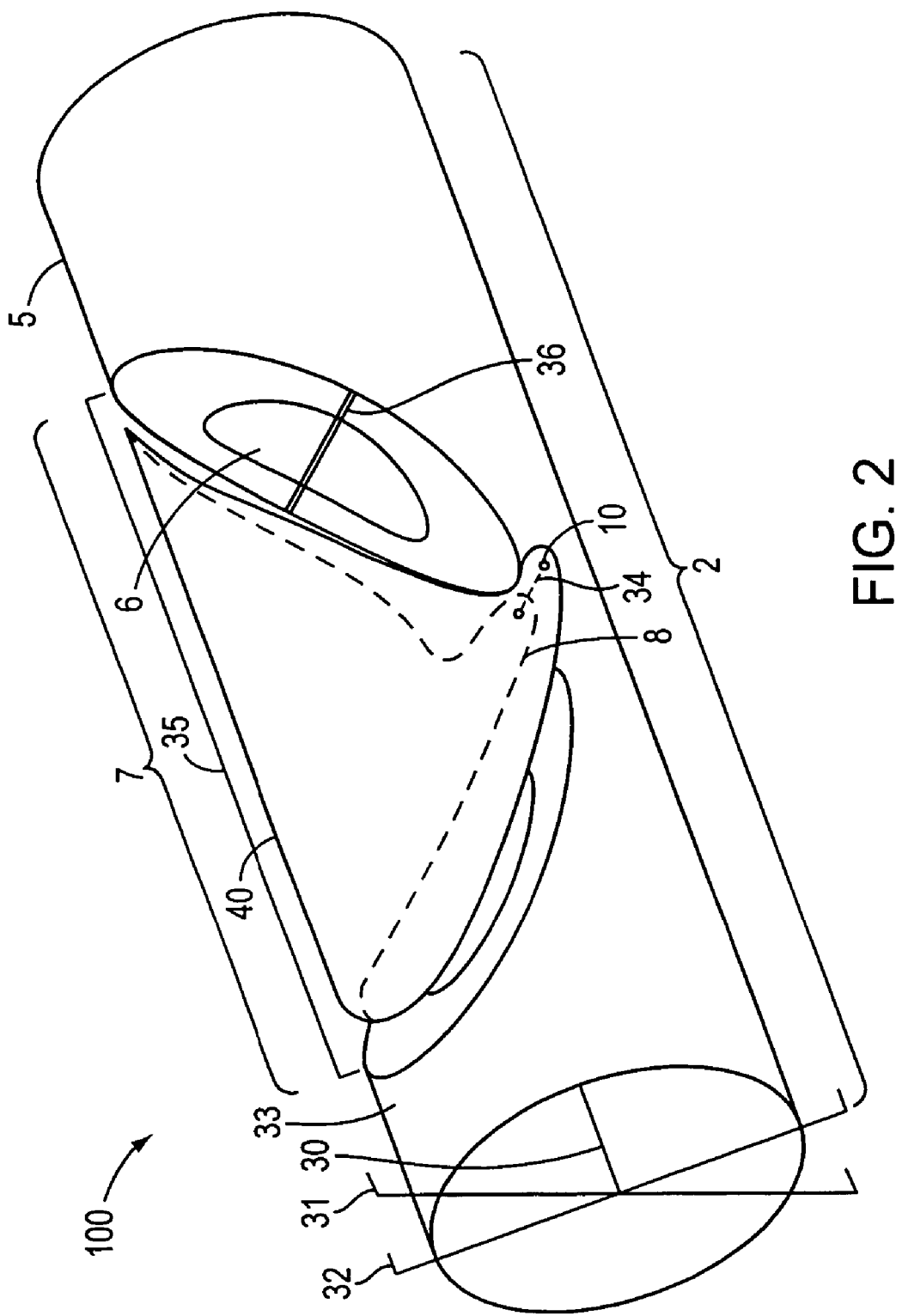
FIG. 2 is a perspective schematic of the second tube at the distal cutting end of the apparatus shown in FIG. 1 including a slot and a lever arm according to an illustrative embodiment of the invention.

FIG. 2 is a perspective schematic of the second tube 5 at the distal cutting end 2 of the apparatus 100 including the slot 7 and the lever arm 8 according to an illustrative embodiment of the invention. In one embodiment, the illustrative second tube 5 is a cylindrical tube including a central longitudinal axis 30. The second tube 5 includes two planes, plane 31 and plane 32, perpendicularly intersecting the central longitudinal axis 30 and perpendicular to each other. In one embodiment, the slot 7 is a longitudinal defect in the wall 33 of the second tube 5. In one embodiment, the slot 7 extends through the entire thickness of the wall 33 to the second lumen 6. In one embodiment, the slot 7 is substantially symmetrical about the plane 31 which longitudinally bisects the slot 7. The length 35 of the slot 7 is in the range of about 0.5 mm to 10 mm, or 1 mm to 3 mm, preferably. The maximum width 36 of the slot 7 is generally equivalent to the external diameter of the second tube. The slot 7 is sized and shaped to receive the lever arm 8.

The illustrative lever arm 8 is generally an inverted U shape in a traverse section, wedge-shaped when viewed from the side, and substantially symmetrical about plane 31. The lever arm 8 pivots about a pivot 10. The axis 34 of the pivot 10 is perpendicular to the axis 30 and parallel to the plane 32. The top 40 of the wedge-shaped illustrative lever arm 8 in a collapsed position is parallel to the longitudinal axis 30 of the second tube 5 and is flush with the outer wall 33 of the second tube 5.

Figure 3:
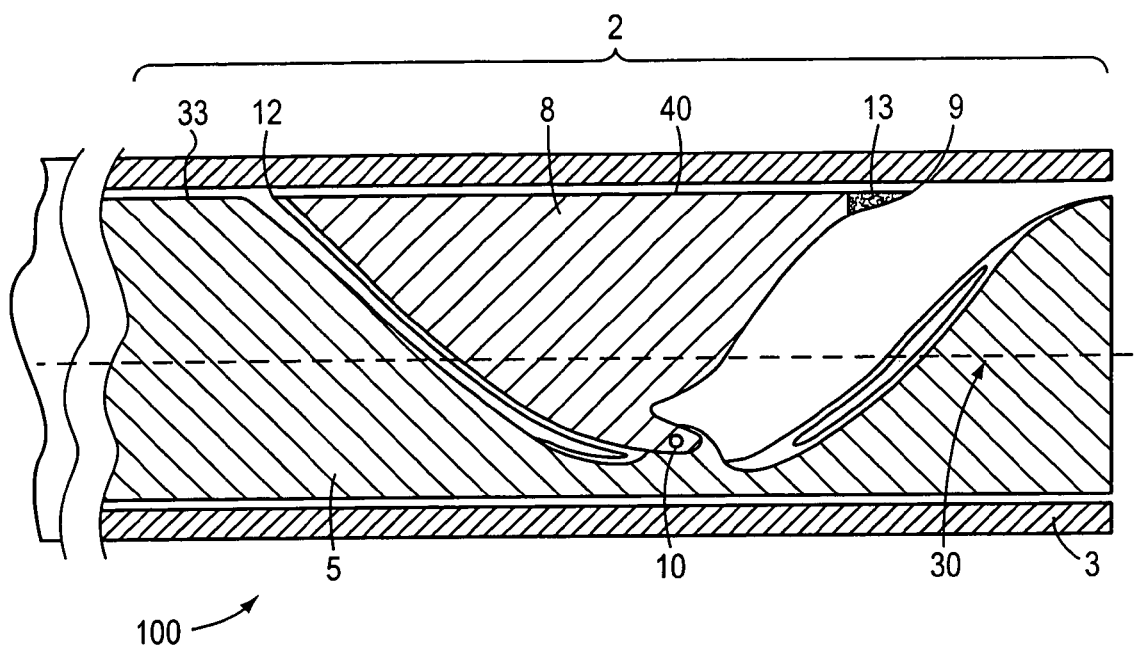
FIG. 3 is an illustrative schematic of the apparatus including a cutaway of the first tube at the distal cutting end to illustrate the lever arm with a cutting edge shown in FIG. 1 according to one illustrative embodiment of the invention.

FIG. 3 is an illustrative schematic of the apparatus 100 including a cutaway of the first tube 3 at the distal cutting end 2 to illustrate the lever arm 8 with a cutting edge 13 shown in FIG. 1 according to one illustrative embodiment of the invention. The lever arm 8 pivots about the pivot 10. The top 40 of the wedge-shaped illustrative lever arm 8 is positioned parallel to the longitudinal axis 30 of the second tube 5 and is flush with the outer wall 33 of the second tube 5. The lever arm 8 includes the pivot 10, a lever arm proximal end 12, and a lever arm distal end 9. A cutting edge 13 is positioned on the top 40 of the lever arm 8 at the lever arm distal end 9 of the lever arm 8. In one embodiment, illustrated in FIG. 3, the cutting edge 13 is a straight edge blade. Alternatively, the cutting edge 13 is tooth-like or pointed such that the cutting edge 13 may pierce and/or fracture a suture.

Figure 4:
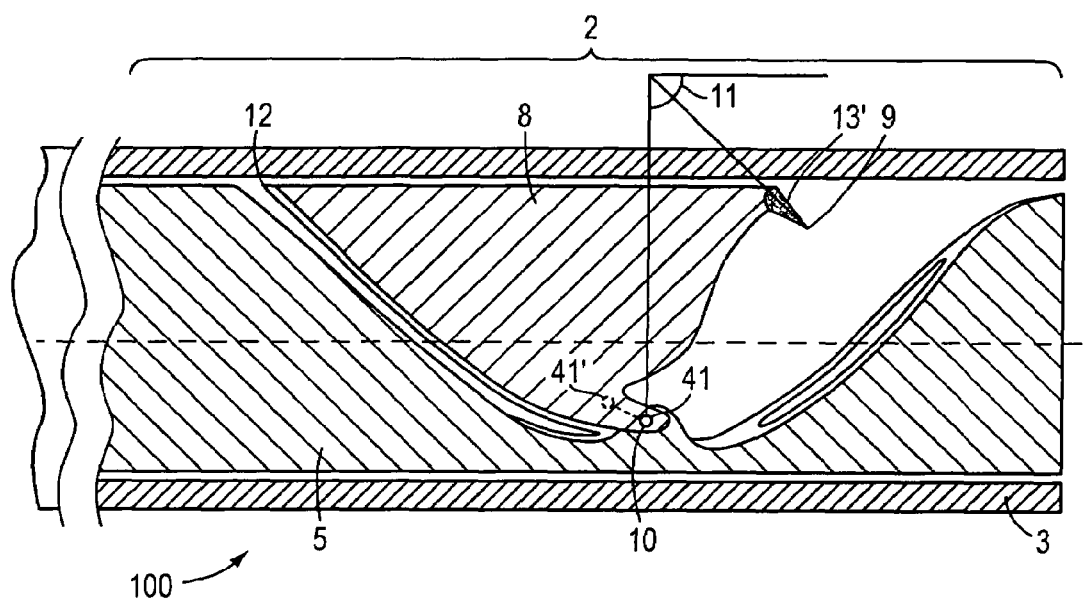
FIG. 4 is an illustrative schematic of the apparatus including a cutaway of the first tube at the distal cutting end to illustrate the lever arm with a cutting edge shown in FIG. 1 according to another illustrative embodiment of the invention.

FIG. 4 is an illustrative schematic of the apparatus 100 including a cutaway of the first tube 3 at the distal cutting end 2 to illustrate the lever arm 8 with a cutting edge 13' shown in FIG. 1 according to another illustrative embodiment of the invention. The illustrative cutting edge 13' biases downward in the direction of the pivot 10 at an angle 11 of about 0 to 90 degrees, preferably about 45 degrees from a line perpendicular to the longitudinal axis of the second tube 5.

With continued reference to FIG. 4, the lever arm 8 includes a pivot 10 according to one illustrative embodiment of the invention. The illustrative pivot 10 pivotably connects the lever arm 8 to the second tube 5. In one embodiment, the pivot 10 with two ends 41, 41' is a transverse rod that passes through a solid portion of the second tube 5 connecting the pivot ends 41, 41' of the lever arm 8 to the second tube 5. The pivot 10 may be located anywhere along the longitudinal axis of the lever arm 8 between the lever arm proximal end 12 and the lever arm distal end 9, preferably located approximately halfway between the lever arm proximal end 12 and the lever arm distal end 9.

Figure 5:
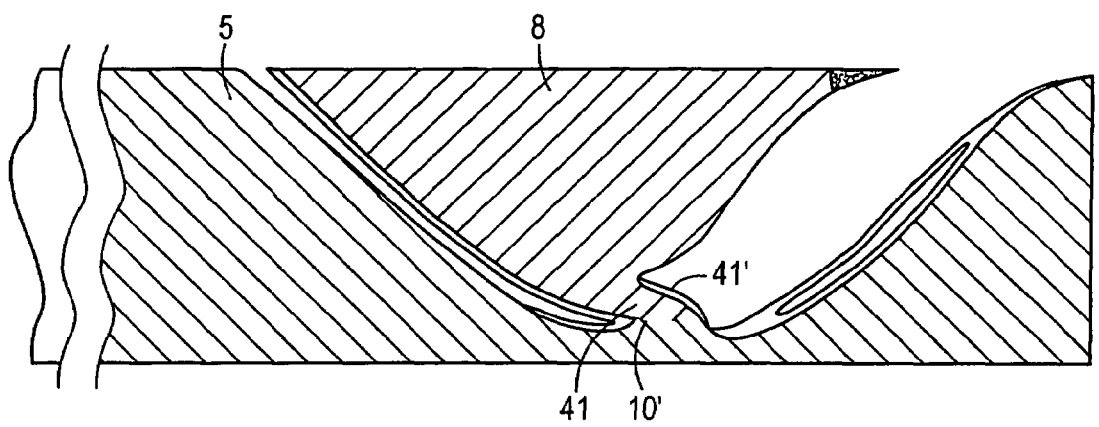
FIG. 5 is an illustrative schematic of the lever arm including a pivot according to another illustrative embodiment of the invention.

FIG. 5 is an illustrative schematic of the lever arm 8 including a pivot 10' according to another illustrative embodiment of the invention. The illustrative pivot 10' pivotably connects the lever arm 8 to the second tube 5. In one embodiment, the pivot 10' is a flexible material connecting the pivot ends 41, 41' of the lever arm 8 to the second tube 5 allowing the lever arm 8 to pivot by flexing the flexible material of the pivot 10'.

Figure 6:
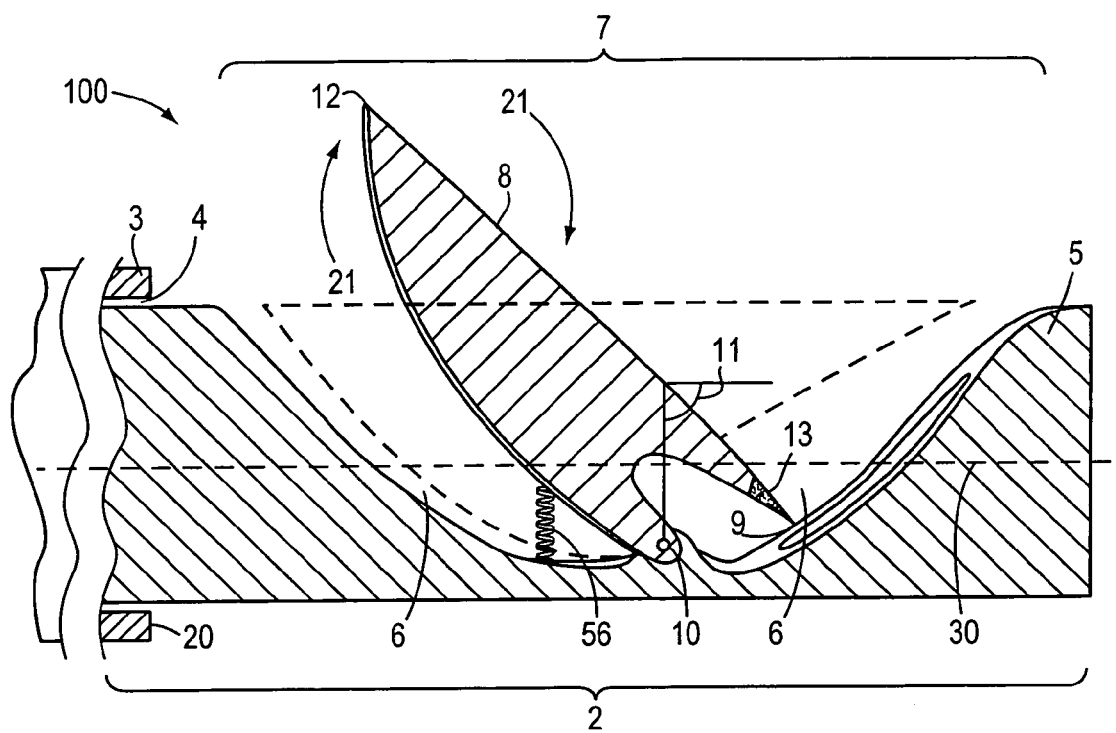
FIG. 6 is an illustrative cutaway schematic of the first tube at the distal cutting end of the apparatus shown in FIG. 1 including a second tube advanced distally from the first lumen of the first tube according to an illustrative embodiment of the invention.

FIG. 6 is an illustrative cutaway schematic of the first tube 3 at the distal cutting end 2 of the apparatus 100 including either a second tube 5 advanced distally from the first lumen 4 of the first tube 3 or alternatively the first tube 3 and first lumen 4 retracted proximally from the second tube 5 according to an illustrative embodiment of the invention. The illustrative slot 7 and the lever arm 8 are extended beyond the distal end 20 of the first tube 3. The slot 7 is sized and shaped to allow the cutting edge 13 to pivot as indicated by arrow 21 into the second lumen 6 of the second tube 5. A biasing mechanism, such as spring 56, urges the lever arm distal end 9 of the lever arm 8 to move from a collapsed position, shown in phantom, to an open position across the longitudinal axis 30 of the second lumen 6. The desired angle 11 of the lever arm 8 relative to a vertical axis perpendicular to the longitudinal axis 30 of the device 100 is in the range of about 0 degrees to about 90 degrees, preferably 45 degrees. As the lever arm 8 pivots on the pivot 10, the lever arm proximal end 12 lifts out of the second lumen 6.

Figure 7:
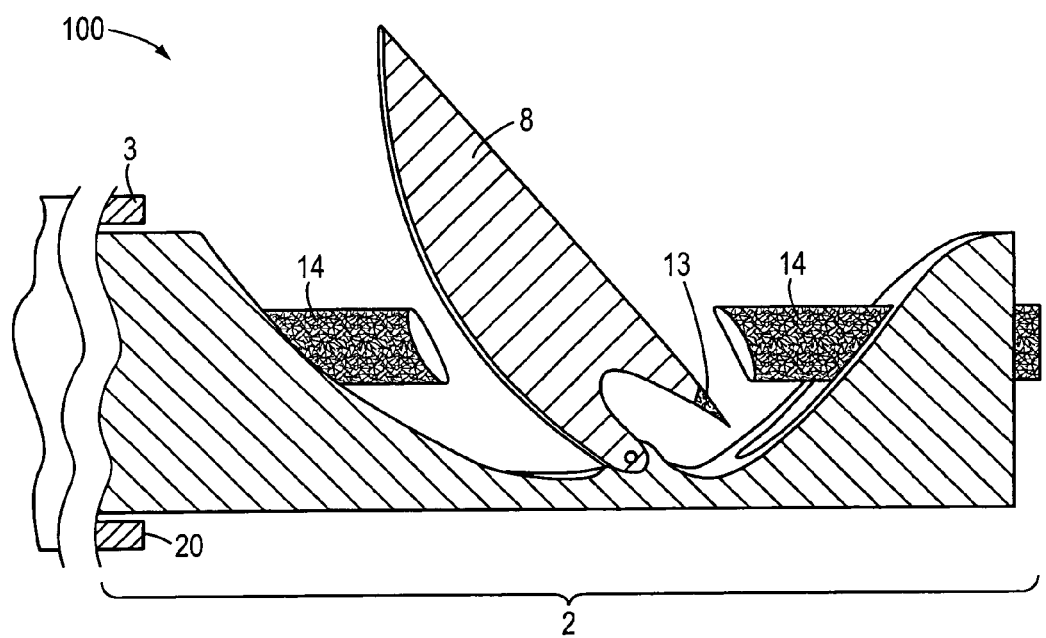
FIG. 7 is a cutaway schematic of the first tube at the distal cutting end of the apparatus shown in FIG. 1 including the lever arm in a cutting position and a severed suture according to an illustrative embodiment of the invention.

FIG. 7 is a schematic of the first tube 3 at the distal cutting end 2 of the apparatus 100 including the lever arm 8 in a cutting position extended distally beyond the distal end 20 of the first tube 3, and a severed suture 14 cut by the cutting edge 13 of the lever arm 8 according to an illustrative embodiment of the invention. The illustrative cutting edge 13 cuts the suture 14 into two separate segments.

Figure 8:
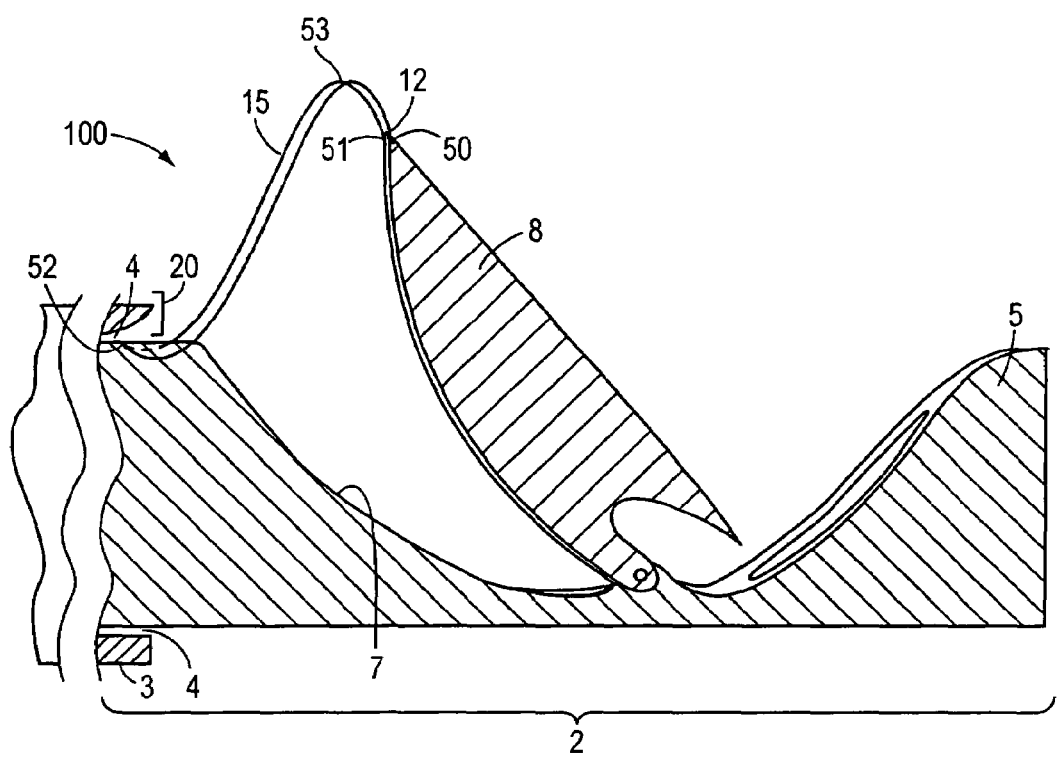
FIG. 8 is a cutaway schematic of the first tube at the distal cutting end of the apparatus shown in FIG. 1 including a return guide in an open position according to an illustrative embodiment of the invention.
Figure 9:
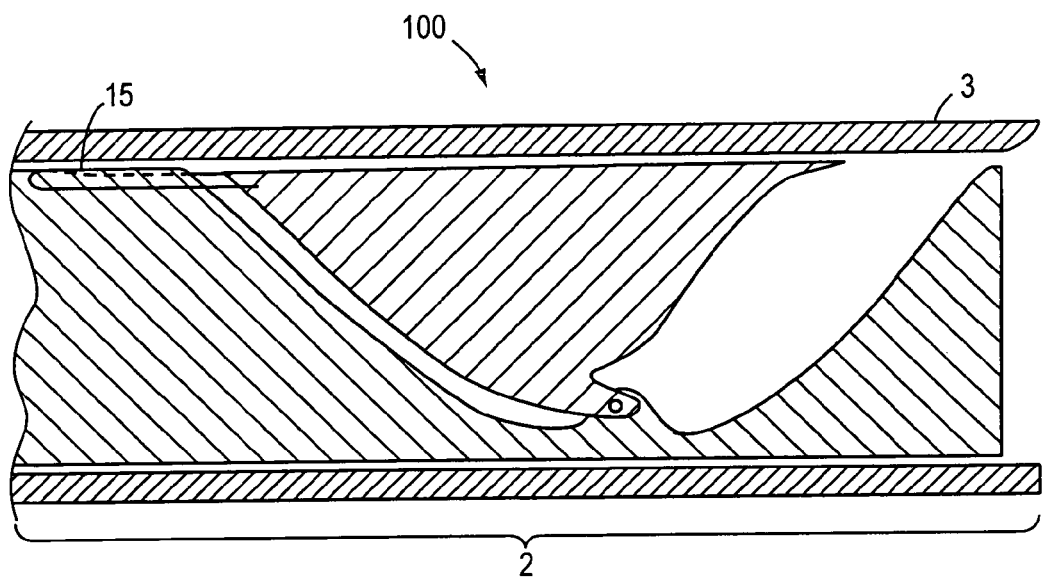
FIG. 9 is a cutaway schematic of the first tube at the distal cutting end of the apparatus shown in FIG. 1 including a return guide in a collapsed position according to an illustrative embodiment of the invention.

FIG. 8 is a cutaway schematic of the first tube 3 at the distal cutting end 2 of the apparatus 100 including a return guide 15 in an open position with the lever arm 8 in a cutting position extended distally beyond the distal end 20 of the first tube 3 according to an illustrative embodiment of the invention. In one embodiment, the return guide 15 is a wire loop as illustrated in FIG. 9. The wire loop 15 includes two ends 50, 51 joined to the proximal end 12 of the lever arm 8 and an apex 52 that extends proximally from the two loop ends 50, 51. The wire loop 15 includes a bend 53. As the second tube 5 is withdrawn into the first tube 3, or the first tube 3 is advanced distally over the second tube 5, the apex 52 of the wire loop 15 slides into the lumen 4 of the first tube 3. As the distal end 20 of the first tube 3 provides the necessary force to compress the wire loop 15 thereby minimizing the bend 53 in the wire loop 15, the proximal end 12 of the lever arm 8 returns to a collapsed position enclosed within the slot 7.

FIG. 9 is a schematic of the first tube 3 at the distal cutting end 2 of the apparatus 100 including a return guide 15 in the collapsed position according to an illustrative embodiment of the invention.

In another aspect, the invention is a method for introducing an implant, such as a septal defect occluder, to an anatomical site in a patient. For example, the invention is a method for implanting a septal occluder to occlude a patent foramen ovale.

Figure 10:
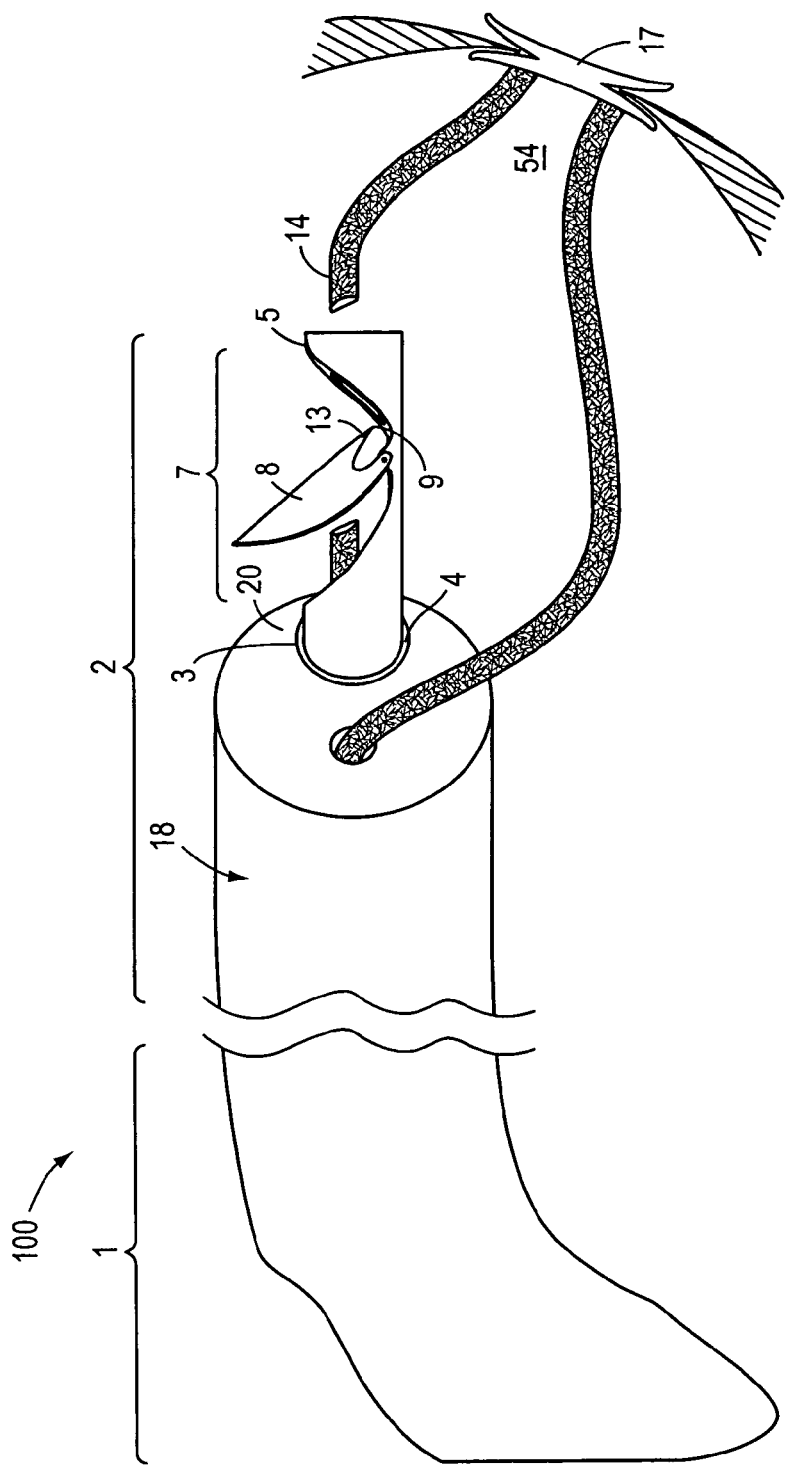
FIG. 10 is a perspective schematic of the apparatus of FIG. 1 including a septal occluder with the distal cutting end of the apparatus positioned in the right atrium of the heart according to an illustrative embodiment of the invention.

For example, FIG. 10 is an illustrative schematic of the apparatus 100 including a septal occluder 17. The distal cutting end 2 of the apparatus 100 is positioned in the right atrium 54 of the heart according to an illustrative embodiment of the invention. The proximal control end 1 is used by an operator to guide the occluder 17 into position at the patent foramen ovale. Once the occluder 17 is positioned as desired, the operator manipulates the control end 1 to urge the second tube 5 distally, or, alternatively, the first tube 3 proximally until the slot 7 and lever arm 8 are extended beyond the distal end 20 of the first tube 3. The cutting edge 13 of the lever arm distal end 9 engages the suture 14. In one embodiment, proximal retraction of the suture 14 draws the suture 14 against the cutting edge 13 thereby severing the suture 14. In another embodiment, further distal advancement of the second tube 5, or, alternatively, withdrawal of the first tube 3 proximally advances the cutting edge 13 through the suture 14, thereby slicing the suture 14 into two segments and releasing the occluder 17. Alternatively, if the cutting edge 13' illustrated in FIG. 4 is used, engagement of the cutting edge 13' with the suture 14 fractures the suture 14 such that it may be segmented with minimal tension applied to the suture 14 by the operator.

Once the occluder 17 is in place as desired and the suture 14 is severed, the short end of the suture 14 is unthreaded from the occluder 17 and drawn through the catheter 18 towards the proximal control end 1. As such, rather than drawing the entire length of the suture 14 that extends from the proximal control end 1 to the occluder 17, only the short length of the segmented suture 14 that extends from the distal cutting end 2 to the occluder 17 is drawn through the occluder 17.

Although the present invention has been described with reference to the preferred embodiments, workers skilled in the art will recognize that changes may be made in form and detail with departing from the spirit and scope of the invention.

What is claimed is:

1. A suture cutting apparatus comprising:
   a distal cutting end section and a proximal control end;
   a first tube extending from said proximal control end to said distal cutting end section and defining a first lumen and
   a second tube comprising a wall, said second tube extending from said proximal control end to said distal cutting end section and located and slideably moveable within the first lumen of said first tube, said second tube defining a second lumen for slidingly receiving a suture;
   a slot located in the wall of the second tube proximal to a distal end of the second tube;
   a pivot located in the slot; and
   a lever arm comprising a proximal end, a distal end, a channel extending from the proximal end to the distal end for passage of the suture, and a cutting edge at the distal end, wherein said lever arm is received within the slot and rotates about the pivot.

2. The apparatus of claim 1 wherein said lever arm is pivotably attached to said slot by a pin.

3. The apparatus of claim 1 wherein said lever arm is pivotably attached to said slot by a flexible material.

4. The apparatus of claim 1 wherein a top of said lever arm is parallel to a longitudinal axis of said second tube when said lever arm is located within the first lumen of said first tube.

5. The apparatus of claim 1 wherein said lever arm forms an angle relative to a longitudinal axis of said second tube when said lever arm is outside the first lumen of said first tube.

6. The apparatus of claim 5 wherein said angle is in the range of about 0° to about 90°.

7. The apparatus of claim 5 wherein said cutting edge is biased to an angle in the range of about 0° to about 90° relative to a line perpendicular to the longitudinal axis of said second tube.

8. The apparatus of claim 5 wherein said cutting edge is substantially perpendicular to the longitudinal axis of said second tube.

9. The apparatus of claim 1 wherein a cross section of the lever arm is generally U shaped.

10. The apparatus of claim 1 further comprising a return guide.

11. The apparatus of claim 10 wherein said return guide is slideably movable within said first tube.

12. The apparatus of claim 1 further comprising a return guide positioned on said lever arm.

13. The apparatus of claim 1 wherein said cutting edge is replaceable.

14. The apparatus of claim 1 further comprising a catheter.

15. The apparatus of claim 1 wherein the lever arm is transitional between a first state inside the first tube and a second state outside the first tube and wherein the lever arm is capable of being rotated within the slot about the pivot such that the distal end of the lever arm encroaches on the second lumen of the second tube and the proximal end of the lever arm extends outside the second tube when the lever arm is in the second state outside of the first tube.

16. The apparatus of claim 15 wherein the channel of the lever arm is co-extensive with the second lumen of the second tube when the lever arm is in the first state inside the first tube.

17. The apparatus of claim 16 wherein the suture passes from the second lumen at the proximal end of the second tube, through the channel, to the second lumen at the distal end of the second tube along the longitudinal axis of the second tube when the lever arm is in the first state inside the first tube.

18. The apparatus of claim 1 wherein the lever arm is attached to the pivot approximately halfway between the proximal end and the distal end of the lever arm.

19. The apparatus of claim 1 wherein the channel is co-extensive with the lumen of the second tube.

20. The apparatus of claim 1 wherein the channel is co-extensive with the lumen of the distal end of the second tube.

21. A suture cutting apparatus comprising:
a distal cutting end section and a proximal control end;
a first tube extending from said proximal control end to said distal cutting end section and defining a first lumen;
a second tube extending from said proximal control end to said distal cutting end section and located and slideably moveable within the first lumen of said first tube, said second tube defining a second lumen for slidingly receiving a suture; and
a lever arm located at the distal end of the second tube and attached to the second tube at a pivot, said lever arm including a cutting edge at its distal end;
wherein the lever arm is constrained to a first state when the lever arm is within the first tube and the lever arm is biased to a second state when the lever arm is outside the first tube, the second state being rotated through an angle about the pivot such that the cutting edge encroaches on the second lumen thereby cutting the suture as the suture is pulled through the second lumen.

* * * * *